(12) United States Patent
Al Otaibi

(10) Patent No.: US 8,733,366 B2
(45) Date of Patent: May 27, 2014

(54) MEDICAL PROTECTIVE COVER

(75) Inventor: Abdullah Mohammad A Al Otaibi, Makkah (SA)

(73) Assignee: Abdullah Mohammad A. Al Otaibi, Makkah (SA)

( * ) Notice: Subject to any disclaimer, the term of this patent is extended or adjusted under 35 U.S.C. 154(b) by 98 days.

(21) Appl. No.: 13/407,703

(22) Filed: Feb. 28, 2012

(65) Prior Publication Data

US 2013/0220347 A1 Aug. 29, 2013

(51) Int. Cl.
*A61F 13/00* (2006.01)

(52) U.S. Cl.
USPC ........... 128/888; 128/846; 128/889; 128/890; 602/41; 602/42; 602/48; 602/54; 2/15; 2/466; 604/174; 604/180; 604/175; 604/179; 604/192

(58) Field of Classification Search
USPC ........... 128/846, 888, 889, 890, 100.1, 105.1, 128/877, 878, DIG. 6, DIG. 26; 602/67, 68, 602/72, 79, 42, 37, 41, 48, 54; 2/15, 466; 604/174, 180, 6.11, 175, 179, 192; 424/449
See application file for complete search history.

(56) References Cited

U.S. PATENT DOCUMENTS

| | | | |
|---|---|---|---|
| 703,290 A | 6/1902 | Mulford | |
| 2,367,690 A * | 1/1945 | Purdy | 128/888 |
| 4,285,338 A | 8/1981 | Lemelson | |
| 4,470,410 A * | 9/1984 | Elliott | 128/877 |
| 4,516,968 A | 5/1985 | Marshall et al. | |
| 4,667,666 A | 5/1987 | Fryslie | |
| 5,116,324 A * | 5/1992 | Brierley et al. | 604/180 |
| D382,966 S | 8/1997 | Haber et al. | |
| D483,491 S | 12/2003 | Grady et al. | |
| 6,827,707 B2 * | 12/2004 | Wright et al. | 604/180 |
| 7,265,256 B2 | 9/2007 | Artenstein | |
| 7,695,444 B1 | 4/2010 | Simmons et al. | |
| 2007/0142784 A1 | 6/2007 | Dikeman et al. | |
| 2008/0208130 A1 | 8/2008 | Furman | |
| 2009/0247965 A1 | 10/2009 | Williams | |

FOREIGN PATENT DOCUMENTS

DE 195 46 809 A1 7/1997

\* cited by examiner

*Primary Examiner* — Patricia Bianco
*Assistant Examiner* — Caitlin Carreiro
(74) *Attorney, Agent, or Firm* — Richard C Litman

(57) ABSTRACT

The medical protective cover includes a semi-ovoid shell configured to cover a wound or intravenous site. The shell is attached to a patient's limb or extremity by a pair of adhesive tabs extending from longitudinal ends of the shell and a plurality of adjustable straps extending laterally from the shell. A plurality of ventilation holes longitudinally extend along lateral edges of the shell to allow passage of air for keeping the covered area dry. Each longitudinal end of the shell includes a pair of tubing ports to facilitate mounting and passage of IV infusion tubing to an IV catheter or cannula. The top of the shell also includes a selectively opened slot that permits passage of a needle for the administration or withdrawal of fluids through an access port of the catheter.

5 Claims, 4 Drawing Sheets

MEDICAL PROTECTIVE COVER

BACKGROUND OF THE INVENTION

1. Field of the Invention

The present invention relates to medical devices, and particularly to a medical protective cover that provides substantial shock resistance, infection prevention and a stable holder for cannulae.

2. Description of the Related Art

Many common medical procedures require some form of bandaging. Some of the more common types of bandaging are for covering wounds or an intravenous injection site. In these situations, the bandage is often held in place by medical tape. As strong as the bonding properties of medical tape may be, they are still prone to external forces and environmental influences. For example, any impact on the bandaged area can potentially reopen healing wounds, trauma and even lead to dislodging of the bandage. In the case of a peripherally inserted catheter and the like, any impact thereon can cause dislodging of the intravenous catheter, or even additional venous damage.

Potential infections in these situations are of utmost concern to medical professionals. Any of the above instances can lead to increased potential of infection and/or contamination. Exposed bandages are also susceptible due to their unhindered exposure to the environment. While it is ideal in most instances to keep bandages dry, exposed bandages can be prone to airborne bacteria and/or unintended moisture. Catheters and intravenous infusion devices, an example of which is a butterfly cannula (commonly referred to as a butterfly needle used as part of an intravenous infusion set), leaves the injection site exposed, leading to many of the potential dangers noted above.

Many different protective covers have been proposed in the medical field. Some offer complete coverage over a bandaged or intravenous site, except for access from a catheter or cannula, but without ventilation. Others provide ventilation, but without access for a catheter or cannula. Still others are complex in construction with an added moisture barrier element, which involves additional costs of manufacture, leading to higher costs for the medical facility. Thus, a medical protective cover solving the aforementioned problems is desired.

SUMMARY OF THE INVENTION

The medical protective cover includes a semi-ovoid, rigid shell configured to cover a wound or intravenous site. The shell is attached to a patient's limb or extremity by a pair of adhesive tabs extending from longitudinal ends of the shell and a plurality of adjustable straps extending laterally from the shell to wrap at least partially around the limb. A plurality of ventilation holes are formed along and near the longitudinal edge of the shell to allow passage of air for keeping the covered area dry. Each longitudinal end of the shell includes a pair of tube holes to facilitate mounting and passage tubes for drip infusions. The top of the shell also includes a selectively opened slot that permits passage of a needle for the infusion or withdrawal of fluids.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
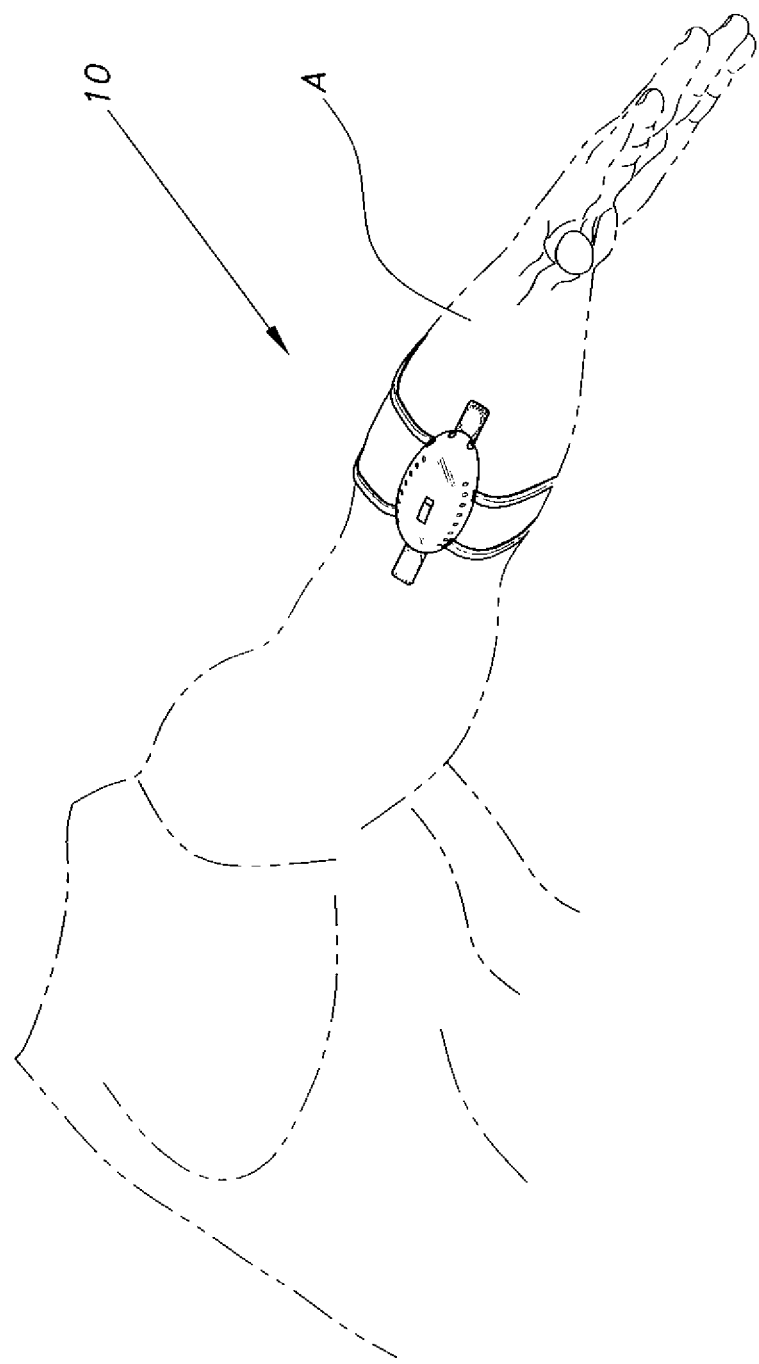
FIG. 1 is an environmental, perspective view of a medical protective cover according to the present invention.
Figure 2:
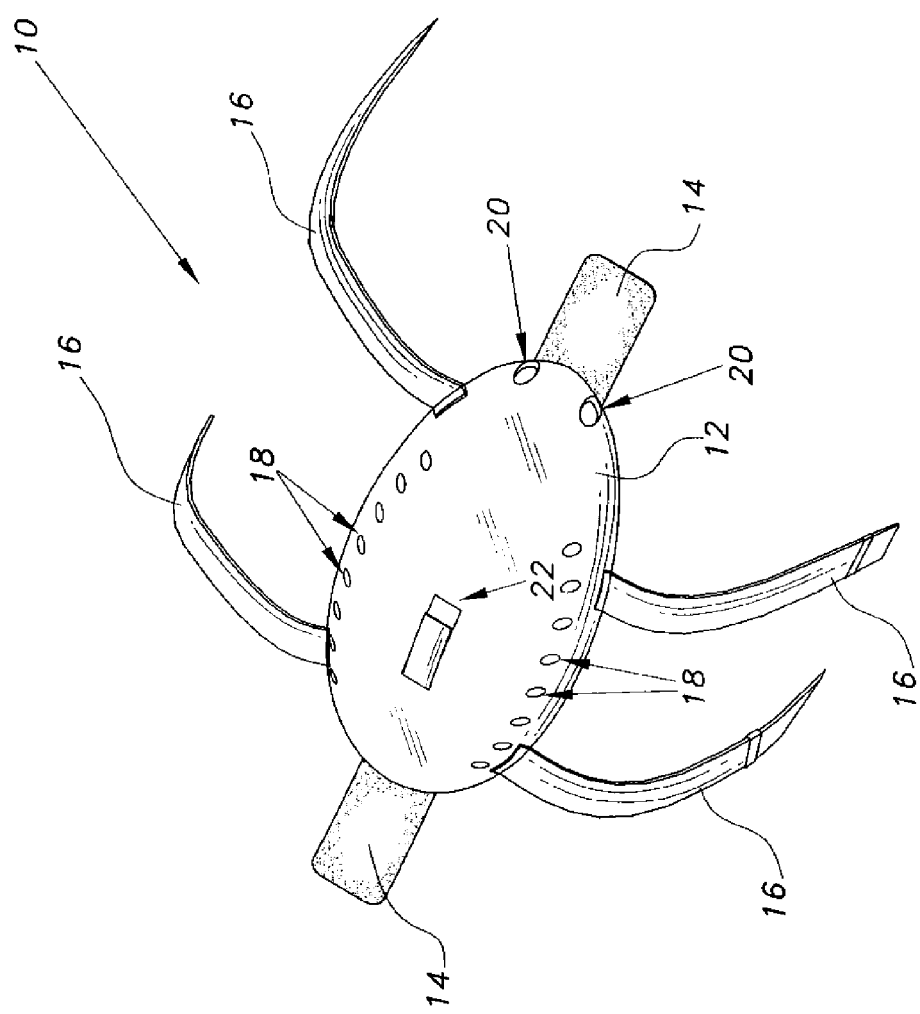
FIG. 2 is a perspective view of the medical protective cover shown in FIG. 1.

The medical protective cover, generally referred to in the drawings by the reference number 10, provides impact protection over a wound (e.g., an open or a bandaged wound or an intravenous site), ventilation, and selective access or mounting for a catheter or cannula, e.g., a butterfly cannula used with an intravenous infusion set. As shown in FIGS. 1 and 2, the medical protective cover 10 includes a rigid shell or body 12 secured to the arm A of a patient (or to the back of the hand or other IV access point) or user by a combination of adhesive tabs 14 and straps 16. The shell 12 is preferably semi-ovoid in shape and constructed from transparent, durable, shockproof plastic. The semi-ovoid shape forms a dome that can cover most wounds and intravenous sites. It is noted that the shell 12 can include other shapes that form a cover in accordance with the teachings described herein. The transparent plastic construction provides impact protection and allows medical practitioners an unobstructed view of the covered area. Additionally, the shell 12 can easily be cleaned, sterilized and reused, which is a cost effective benefit in light of ever increasing healthcare costs.

The adhesive tabs 14 and the straps 16 securely mount the shell 12 onto the arm A, the back of the hand, or any other anatomical part of the user or patient, usually the limbs or extremities. The adhesive tabs 14 extend from longitudinal ends of the shell 12, and can be constructed similar to household band-aids, the adhesive side normally being covered by a release strip prior to use. The adhesive tabs 14 can be flexible or stiff, depending on the materials used to construct the same. Preferably, the tabs 14 are made from flexible plastic. A laminate construction, such as cardboard or cardboard and plastic, is also feasible. Once attached, the adhesive tabs 14 help prevent undesirable movement of the shell 12, mainly in the longitudinal direction, and to a degree, also laterally, especially in the event of an inadvertent impact. When reused, the tabs 14 can be secured to the patient's limb with medical tape. The straps 16 extend laterally from the shell 12 and may be adhesive straps that extend at least partially around a patient's hand or arm, or can be a belt with overlapping ends that forms a continuous loop around the patient's hand or limb to securely fasten the shell 12. A variety of adjustable belt constructions can be used, such as one with hook and loop type fasteners, loop straps with buckles and adjustment holes, or the like.

Figure 3:
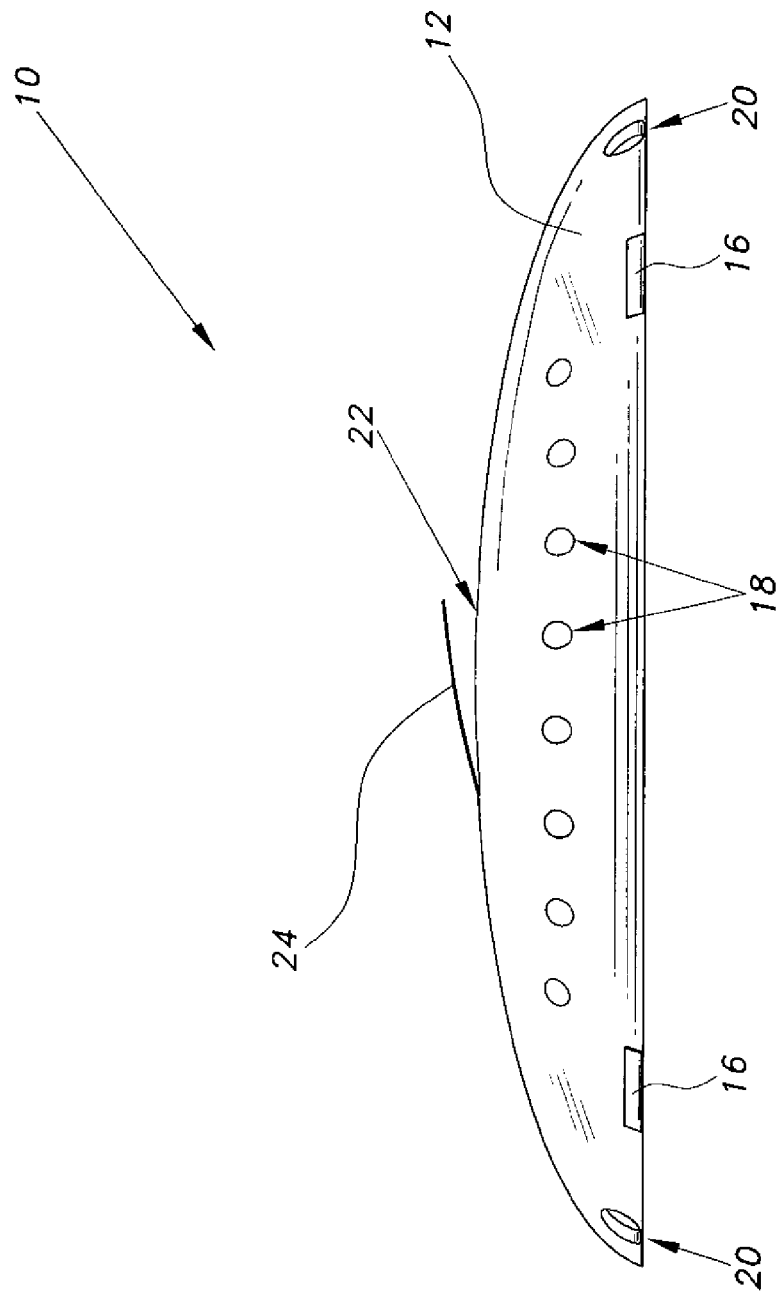
FIG. 3 is a side view of the medical protective cover shown in FIG. 1.
Figure 4:
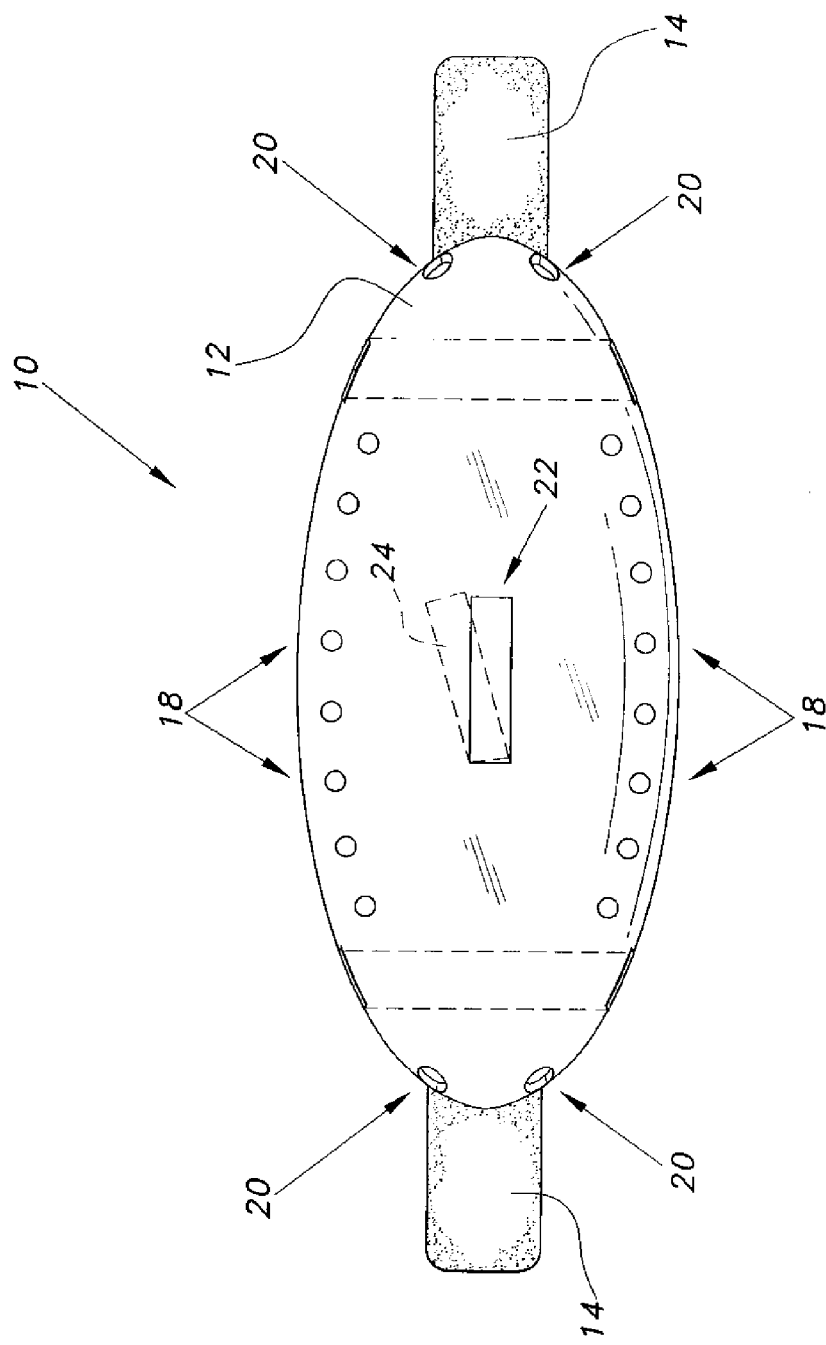
FIG. 4 is a top view of the medical protective cover shown in FIG. 1.

Besides the impact resistance and visual aspects, the shell 12 also includes various features for ventilation, installation of IV tubing for drip infusions, and access for needles for administration of medications or withdrawal of blood samples, etc. As shown in FIGS. 2-4, the shell 12 includes a plurality of ventilation holes 18 disposed in a pair of opposite longitudinally extending rows arranged adjacent the outer lateral edges of the shell 12. The ventilation holes 18 are preferably small, yet provide sufficient passage of air to maintain a dry environment for the covered area. Each row of ventilation holes 18 can include any desired number of holes.

Such ventilation is especially desirable for inflamed wounds that should not be covered by bandages and the like.

Each longitudinal end of the shell 12 also includes a pair of spaced tube holes or ports 20 formed thereon. The tube ports 20 permit installation and passage of tubing for administering medication by drip infusion.

The top of the shell 12 further includes an access aperture or slot 22. The slot 22 permits passage of a hypodermic needle for bolus injections of medication or withdrawal of fluid samples through a heplock or other access port in the indwelling catheter or cannula. The slot 22 can be selectively accessed by operation of a hinged lid or cover 24 that normally seals the slot 22. The hinge can be a living hinge, and the lid 24 can be secured to the slot 22 by a snap fit engagement. Alternatively, the lid 24 may slidably cover the access slot 22.

Thus, it can be seen that the medical protective cover 10 provides impact protection and protection against potential contamination by covering the wound or intravenous site. The ventilation holes 18 insure that the covered area remains dry, and the tubing ports 20 and the access slot 22 permit installation of infusion tubing and needle access to cannula and catheter ports, as required.

It is to be understood that the present invention is not limited to the embodiments described above, but encompasses any and all embodiments within the scope of the following claims.

I claim:

1. A medical protective cover, comprising:
    a dome-shaped rigid shell dimensioned and configured for covering an intravenous access site on a patient's body, including an intravenous catheter left inserted in the patient, the dome-shaped rigid shell being transparent to facilitate visual inspection of an area covered by the dome-shaped rigid shell, the dome-shaped rigid shell being elongated to define a longitudinal axis, the dome-shaped rigid shell having:
    a plurality of ventilation holes formed therein for permitting air passage to dry the covered area;
    a plurality of tubing ports formed in opposite, longitudinal ends of the dome-shaped rigid shell, the plurality of tubing ports being adapted to receive intravenous infusion tubing therethrough; and
    a selectively covered access slot formed on top of the dome-shaped rigid shell, the access slot being elongated and extending along the longitudinal axis, the access slot permitting the passage of a needle therethrough for administration and withdrawal of fluid through the intravenous catheter;
    a lid selectively covering the access slot, wherein the lid is attached to the dome-shaped rigid shell;
    a pair of adhesive tabs extending only from opposite longitudinal ends of the dome-shaped rigid shell and extending along the longitudinal axis, each pair of adhesive tabs having an adhesive side; and
    a plurality of adjustable straps being attached to and extending laterally and directly from each side of the dome-shaped rigid shell, the plurality of adjustable straps being adapted for at least partially wrapping around a user's body to secure the shell thereon;
    wherein the dome-shaped rigid shell provides impact resistant and contaminant protection over the covered area.

2. The medical protective cover according to claim 1, wherein said dome-shaped rigid shell is semi-ovoid in shape.

3. The medical protective cover according to claim 2, wherein said plurality of ventilation holes comprise two rows of ventilation holes extending longitudinally adjacent lateral edges of said dome-shaped rigid shell.

4. The medical protective cover according to claim 1, wherein said dome-shaped rigid shell is made from plastic.

5. The medical protective cover according to claim 1, wherein said plurality of adjustable straps comprise mating fasteners adapted for forming a continuous, adjustable loop around a patient's extremity.

\* \* \* \* \*